US012778872B2

(12) United States Patent
Sato

(10) Patent No.: US 12,778,872 B2
(45) Date of Patent: Nov. 3, 2026

(54) SYNTHESIZED MOLECULE OF SOLKETAL ESTERS FROM PALM KIT OIL AND GLYCERIN FOR COSMETIC AND AGRICULTURAL FORMULATIONS

(71) Applicant: NUOL Green Chemistry LLC, Little Falls, MN (US)

(72) Inventor: Setsuo Sato, Piracicaba (BR)

(73) Assignee: Nuol Green Chemistry LLC, Little Falls, MN (US)

( * ) Notice: Subject to any disclaimer, the term of this patent is extended or adjusted under 35 U.S.C. 154(b) by 116 days.

(21) Appl. No.: 18/409,301

(22) Filed: Jan. 10, 2024

(65) Prior Publication Data

US 2024/0225981 A1 Jul. 11, 2024

(30) Foreign Application Priority Data

Jan. 10, 2023 (BR) ...................... 10 2023 000441 5

(51) Int. Cl.

| | |
|---|---|
| ***A61K 8/49*** | (2006.01) |
| ***A01N 25/04*** | (2006.01) |
| ***A01P 3/00*** | (2006.01) |
| ***A01P 7/04*** | (2006.01) |
| ***A01P 13/00*** | (2006.01) |
| ***A61Q 1/14*** | (2006.01) |
| ***A61Q 15/00*** | (2006.01) |
| ***A61Q 17/04*** | (2006.01) |

(52) U.S. Cl.

CPC ............ *A61K 8/4973* (2013.01); *A01N 25/04* (2013.01); *A01P 3/00* (2021.08); *A01P 7/04* (2021.08); *A01P 13/00* (2021.08); *A61Q 1/14* (2013.01); *A61Q 15/00* (2013.01); *A61Q 17/04* (2013.01); *A61K 2800/49* (2013.01); *A61K 2800/874* (2013.01)

(58) Field of Classification Search

None

See application file for complete search history.

(56) References Cited

U.S. PATENT DOCUMENTS

| | | | |
|---|---|---|---|
| 5,783,173 | A | 7/1998 | Bonda et al. |
| 7,166,739 | B2 | 1/2007 | Walele et al. |

FOREIGN PATENT DOCUMENTS

| | | | | |
|---|---|---|---|---|
| BR | PI0603912 | A | 5/2008 | |
| BR | PI0703673 | A2 | 5/2009 | |
| BR | 102013010477 | A2 | 11/2015 | |
| BR | 102012001584 | A2 | 5/2018 | |
| WO | WO-8605186 | A1 * | 9/1986 | ............... C07H 9/04 |

* cited by examiner

*Primary Examiner* — Dominic Lazaro

(74) *Attorney, Agent, or Firm* — Sterne, Kessler, Goldstein & Fox P.L.L.C.

(57) ABSTRACT

It refers to a new group of solketal monoesters having excellent solubility power in sunscreens, excellent emollient properties, spreadability and ease of preparing stable aqueous formulas, completely non-toxic, without characteristics that generate eye or skin irritation, which allows its use as a solubilizer and emollients in cosmetic formulations for body use, facial sunscreens, makeup removers and a component for use in "roll on" deodorants. The proposed molecule is obtained from palm kernel oil, coconut oil, macauba oil and glycerin as a solubilizer in the form of cocoyl solketal ester, more particularly solketal monoester prepared from oils and/or fatty acids of coconut, babassu, palm kernel.

20 Claims, No Drawings

SYNTHESIZED MOLECULE OF SOLKETAL ESTERS FROM PALM KIT OIL AND GLYCERIN FOR COSMETIC AND AGRICULTURAL FORMULATIONS

CROSS REFERENCE TO RELATED APPLICATION

The present invention claims the benefit of priority to Brazilian Patent Application No. 10 2023 000441 5 filed on Jan. 10, 2023 with the Brazilian Patent Office, the entire contents of which are incorporated herein by reference in its entirety.

TECHNICAL FIELD

The invention is based on the development of a new molecule based on the solketal ester of palm kernel oil, coconut oil, palm oil, which chemical structure confers a high solubilizing power combined with excellent wetting, emollience, spreadability and softness.

Soluble in oils and non-polar substances with excellent emulsibility power, its composition is entirely based on natural and renewable raw materials.

These properties make these products excellent candidates as components in cosmetic and personal care formulations, such as sunscreens, body creams, antiperspirants and deodorants, and also in agricultural formulations where the same properties are desired by leaves, trunks and roots.

BACKGROUND OF THE INVENTION

The products most used in the applications mentioned above are those that can solubilize solar ultraviolet radiation protection filters such as dibenzoylmethane derivatives, mainly 4-(1,1-dimethylethyl)-4-methoxydibenzoylmethane (PARSOL® 1789) and cinnamic acid derivatives, particularly 2-ethylhexyl paramethoxycinnamate and octylcinnamate, to prepare liquids with a stable composition, good spreadability, non-irritability, resistant to washing and, mainly, liquids that provide a feeling of comfort on human skin.

Esters of benzoic acid made with carbonic chain alcohols from C1 to C18, especially those with a short chain, such as methyl benzoate, are quite common; dicaprylic ethers, fatty acid esters, such as isopropyl myristate, isopropyl palmitate, octyl octoate, esters.

Esters produced from linear or branched carbon chain carboxylic acids containing 8 to 18 carbons and acetals produced from glycerin reacted with ketones or aldehydes are the target end products of the present invention.

Due to the broad variety of existing products, the products are selected in the vast majority of cases based on the performance, cost and availability of the product in each region. Products from renewable sources may, in some applications, have greater added value than those from petrochemical sources.

Formulations are made using more than one product to obtain the desired effects for each specific need, for example, the use of natural antioxidants in cosmetic formulations that use fatty esters as oil-giving agents for the skin. In the industrial field, products and formulations containing lubricity, spreadability, anti-corrosion protection, plasticity, adhesiveness, solvency, hydrophilicity and hydrophobicity effects are highly demanded by the market.

The cosmetic industry, in the production of creams, shampoos, and sunscreens, uses esters of fatty acids, such as octyl stearate, isopropyl palmitate, cetyl palmitate, combined with tocopherols to obtain an oily effect and skin and hair protection.

The domestic and industrial hygiene industry frequently uses glycols such as butyl glycol or its acetate, monoethylene glycol, monoethylene glycol ether, in cleaning formulations such as detergents, soaps, multipurpose cleaners.

In the agricultural industry, the use of ethylhexyl lactate, lactamides, toluol, xylene, methyl caprylate, methyl oleate, methyl linoleate, isoparaffins, triacetin, isophorones, citric acid esters, lactic acid esters, maleic acid diesters, propylene glycol and its diesters, dimethicone, phthalic acid diesters, etc.

Sunscreens and a variety of additives used in cosmetic formulations are solid substances that are difficult to solubilize. Non-toxic products that solubilize and provide good spreadability are the most desired for this type of market. They normally use several components seeking the most balanced formula considering the regions, their different ethnicities, climates, and economic power so that a greater number of users can benefit from a safe and accessible formula.

Document U.S. Pat. No. 5,783,173 describes sunscreens and their stable formulations that use benzoic acid derivatives as a solubilizer and emollient.

Document BR102013010477 describes the development of new benzoic acid esters using branched alcohols which purpose is the formulation of sunscreens, deodorants, antiperspirants.

Document U.S. Pat. No. 7,166,739 B2 also describes new esters for cosmetic purposes.

The objective of the present invention is to create, with glycerin derivatives, motivated by the growing global production of the same, new sunscreen solubilizing agents and agricultural active ingredients since they are the components that are most difficult to solubilize.

OBJECTIVES OF THE INVENTION

It is considered that the global esthetic market is expected to overcome the US$21 billion mark up to 2024, growing at an annual rate of 12.2% during this period, according to the 2018 report from the company Market Research Engine.

This result is due to reasons such as greater awareness among consumers; health benefits of medical esthetic procedures; increase in the elderly population; change in preference from surgical to non-surgical procedures; and advancement in laser technology.

The emollient is a non-greasy oily and lipid compound, which hydrates and restores the oiliness of dry skin. It prevents water evaporation through the formation of an occlusive film, generating the activation of local circulation.

The emollient fills the "spaces" in the skin cells, so the product is easily spread. Humectants, on the other hand, retain around 70% of the water, making it ideal to be used when the skin is damp, so as not to lose moisture easily.

Moisturizers using occlusive agents, in turn, form a layer that slows water loss and leaves the skin looking brighter and stickier.

A desired molecule for the purpose of this patent would have to have the following properties:

1.—high solubilization power.

2.—excellent hydration.

3.—spreadability.

4.—hydration of skin and hair.

5.—formation of a barrier on the skin.

6.—washability resistance.

7.—microbial activity.

8.—chemical and thermal stability.

9.—do not interfere with other active ingredients.

10.—be of natural origin.

11.—biodegradable.

12.—competitive cost.

The objective of the present invention is to create a product to meet the aforementioned requirements of this molecule.

DESCRIPTION OF THE INVENTION

The present invention has as its reference the document BR 10 2013 010477 9 requested by the same applicant which describes the synthesis and applications of acetal esters, which was previously described in patent PI 0603912-0 and PI0703673-6, where the acetals can be formed in situ, that is, acetals and esters are formed at the same time, wherein the glycerin used is the purified glycerin obtained according to patent BR 1020120015846, although distilled glycerin or market standard treated blonde glycerin can be used in the synthesis of the product claimed in the present invention. Acetals in this case are synthesized using aldehydes (from carbons 1 to 8).

The present invention is directed to the use of a specific group of solketal esters for use in personal use formulations. It has been proven that solketal esters containing 12 to 24 total carbons originating from the carbon chain of the carboxylic acid plus the carbons coming from solketals have excellent solubilization power, are not irritating to human skin or eyes, are non-toxic, have excellent chemical and hydrolytic stability, good lubricity, low oiliness, and generate stable emulsions and aqueous dispersions. These are the initial requirements for candidates for the chemical group called solubilizers and emollients in the cosmetic industry.

These esters are represented by the chemical structure below:

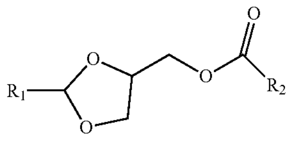

glyceryl acetal esters

R1 represents 3 to 8 carbons.

R2 represents 8 to 18 carbons.

Table 1 below shows the basic physical and chemical characteristics of cocoyl glyceryl solketal used in solubilization tests and sunscreen formulations:

TABLE 1

(COCOIL GLYCERYL SOLKETAL-LOT HNC214).

| | |
|---|---|
| Aspect | Transparent liquid |
| Active substance | 99.8% |
| odor | characteristic |
| Freezing point (Celsius) | −3° C. |
| Flash point (Celsius) | 155 |
| Density at 25° C. | 0.925 |
| viscosity @ 40 Celsius | 8.2 centistokes |
| Acid value (mgkoh/g) | 0.2 |
| Saponification index (mgkoh/g) | 178 |
| Color Gardner | <1 |

Table 2 below shows the solubility of 3 commercially available sunscreens using cocoyl glyceryl acetal as a solubilizing agent.

TABLE 2

SOLUBILITY OF 3 SOLAR FILTERS.

| Name of sun protection filter | Solubility at 25° C. grams/ 100 grams of cocoyl glyceryl solketal |
|---|---|
| Ethylhexyl Triazone | 16.0 |
| Diethylamino hydroxybenzoyl hexyl benzoate | 18.0 |
| 4-(1,1-dimethylethyl)-4-methoxydibenzoylmethane | 14.0 |

In oral and acute toxicity tests, the product was classified as class 5 (non-toxic) according to GHS standards—globally harmonized classification for chemical substances and mixtures.

In eye irritation tests, the product was classified as non-irritating according to OECD and GHS standards.

In skin irritation tests, the product was classified as non-irritating in 2 tests according to OECD and GHS standards, wherein one of the tests shows mild dermal irritation.

Two new batches of cocoyl glyceryl solketal were sent to confirm dermal irritation tests.

In the following examples, the substance proposed in the invention, Cocoyl glyceryl solketal was tested in formulations of ultraviolet radiation protective body lotion (example 1), oil-free facial sunscreen (example 2), makeup remover (example 3) and antiperspirant deodorant formulation (example 4), all being compared with products commercially used on the market: C12-C15 Alkyl Benzoate, Dibutyl adipate, dicaprylyl carbonate.

EXAMPLE 1

TABLE 3

BODY LOTION SPF 30

| Phase | Composition-INCI names | Test A | Test B | Test C | Test D |
|---|---|---|---|---|---|
| I | Xanthan Gum | 0.10 | 0.10 | 0.10 | 0.10 |
| I | Glycerin | 1.00 | 1.00 | 1.00 | 1.00 |
| II | Disodium EDTA | 0.05 | 0.05 | 0.05 | 0.05 |
| II | Acrylates/Beheneth-25 Methacrylate Copolymer | 0.50 | 0.50 | 0.50 | 0.50 |
| II | Water | 100 | 100 | 100 | 100 |
| III | Diethylamino Hydroxybenzoyl Hexyl Benzoate | 5.50 | 5.50 | 5.50 | 5.50 |
| III | Titanium Dioxide (and) Hydrated Silica (and) Dimethicon/Methicone Copolymer (and) Aluminum Hydroxide. | 2.00 | 2.00 | 2.00 | 2.00 |
| III | Ethylhexyl Methoxycinnamate | | 9.00 | 9.00 | 9.00 |
| III | Cocoyl Glyceryl Solketal | 3.00 | — | — | — |
| III | C12-C15 Alkyl Benzoate | — | 3.00 | — | — |
| III | Dibutyl Adipate | — | — | 3.00 | — |
| III | Dicaprylyl Carbonate | — | | | 3.00 |
| III | Caprylic Capric Triglyceride | 3.00 | 3.00 | 3.00 | 3.00 |
| III | Cetearyl Alcohol | 2.00 | 2.00 | 2.00 | 2.00 |
| III | Glyceryl Stearate | 2.00 | 2.00 | 2.00 | 2.00 |
| III | Sodium Cetearyl Sulfate | 2.00 | 2.00 | 2.00 | 2.00 |

TABLE 3-continued

| BODY LOTION SPF 30 | | | | | |
|---|---|---|---|---|---|
| Phase | Composition-INCI names | Test A | Test B | Test C | Test D |
| III | BHT | 0.10 | 0.10 | 0.10 | 0.10 |
| IV | Aminomethyl Propanol | qs | qs | qs | qs |
| V | Methylene Bis Benzotriazolyl Tetramethylbutylpheno, aqua, Decylglucoside, Propylene Glycol, Xanthan Gum. | 0.30 | 0.30 | 0.30 | 0.30 |
| V | Aqua | 0.30 | 0.30 | 0.30 | 0.30 |
| VI | Phenoxyethanol (and) Methylparaben (and) Ethylparaben (and) Propylparaben (and) Butylparaben (and) Isobutylparaben | 0.50 | 0.50 | 0.50 | 0.50 |
| VI | Fragrance | 0.60 | 0.60 | 0.60 | 0.60 |

Process:

1.—Weigh the components of phase I, add Phase II and heat at 80-85° C.
2.—Weigh the phase III components, homogenize and heat at 80-85° C.
3.—Pour phase I+II over III under constant stirring.
4.—Add Phase IV under stirring until pH=6.5-7.0, when a homogeneous emulsion will form.
5.—Separately, pre-mix Phase V and when the temperature is below 40° C., add it to the emulsion while stirring.
6.—Add the components from Phase VI, one by one, and homogenize. Adjust the pH (6.5-8.5) if necessary.

Sensory Assessment—Purpose

Sensory evaluation is a valuable tool for describing creams, lotions, oils or other compounds from a sensory point of view.

Various parameters are evaluated by a trained panel under usage conditions.

Along with other physical methods (Corneometer, TEWL) it helps to describe the claims of the cosmetic application.

Procedure:

1.—Air-conditioned room 21-24° C.
2.—Trained panel with 11 volunteers.
3.—Assessment is initially carried out 1 minute and 3 minutes after applying the product.
4.—Apply 0.50 g of the test product to the forearm and rub it with the opposite hand, using the 4 fingers.
5.—Spreadability, absorption, oiliness, softness and smoothness are evaluated. We used scales from 1 to 5; where 1=Bad and 5=Excellent.

Formulations B, C and D were submitted to the sensory panel, compared to formula A, where the results are shown in the example in table 4 below:

TABLE 4

| EXAMPLE 1 SENSORY PANEL OF FORMULATIONS B, C and D WITH FORMULA A | | | | |
|---|---|---|---|---|
| Assessment | Test A | Test B | Test C | Test D |
| Spreadability | 4 | 2 | 3 | 4 |
| Absorption | 5 | 3 | 3 | 4 |
| Oiliness | 5 | 3 | 4 | 4 |
| Softness | 4 | 4 | 4 | 4 |
| Smoothness | 5 | 3 | 4 | 4 |

The results show that in this formulation, sensory tests were superior to market products.

EXAMPLE 2

TABLE 5

| EXAMPLE 2 OIL-FREE FACE PROTECTOR | | | | | |
|---|---|---|---|---|---|
| Phase | Composition-INCI names | Test 1 | Test 2 | Test 3 | Test 4 |
| I | Diethylamino Hydroxybenzoyl Hexyl Benzoate | 5.00 | 5.00 | 5.00 | 5.00 |
| I | Ethylhexyl Methoxycinnamate | 8.50 | 8.50 | 8.50 | 8.5 |
| I | Cocoyl Glyceryl Solketal | 2.00 | — | — | — |
| I | C 12-C15 Alkyl Benzoate | — | 2.00 | — | — |
| I | Dibutyl Adipate | — | — | 2.00 | — |
| | Dicaprylyl Carbonate | — | — | — | 2.00 |
| I | Sodium Acrylates copolymer and Paraffinum Liquid and PPG-1 Trideceth-6 | 3.00 | 3.00 | 3.00 | 3.00 |
| II | Disodium EDTA | 0.05 | 0.05 | 0.05 | 0.05 |
| II | Water | 100 | 100 | 100. | 100 |
| III | Methylene Bis Benzotriazolyl Tetramethylbutylphenol, aqua, Decylglucoside, Propylene Glycol, Xanthan Gum. | 6.0 | 6.00 | 6.00 | 6.00 |
| III | Aqua | 6.00 | 6.00 | 6.00 | 6.00 |
| IV | Phenoxyethanol and Methylparaben and Ethylparaben and Propylparaben and Butylparaben and Isobutylparaben | 0.50 | 0.50 | 0.50 | 0.50 |
| IV | Cyclomethicone | 3.00 | 0.50 | 0.50 | 0.50 |
| IV | Aluminum Starch Octenylsuccinate | 3.00 | 3.00 | 3.00 | 3.00 |
| IV | fragrance | 0.30 | 0.30 | 0.30 | 0.30 |

Procedure:

1.—Mix Phase I and Phase II and heat to 80-85° C.

2.—Mix them under constant stirring until an emulsion is formed.

3.—Pre-mix Phase III and when the temperature is below 40° ° C., add to the emulsion under constant stirring.

4.—Add the Phase IV components, one by one, and homogenize. Adjust the pH (6.5-8.5) if necessary.

Formulations 2, 3 and 4 were submitted to the sensory panel, compared to formula 1, where the results are shown in the table below. The protocol used was the same as described above, used in the body lotion:

TABLE 6

SENSORY PANEL OF FORMULATIONS 2, 3 and 4 WITH FORMULA 1

| Assessment | Test 1 | Test 2 | Test 3 | Test 4 |
|---|---|---|---|---|
| Spreadability | 5 | 3 | 3 | 4 |
| Absorption | 4 | 3 | 4 | 4 |
| Oiliness | 5 | 3 | 4 | 4 |
| Softness | 4 | 4 | 4 | 4 |
| Smoothness | 5 | 3 | 4 | 4 |

EXAMPLE 3

TABLE 7

EXAMPLE 3 MAKE UP REMOVER

| Phase | Composition-INCI names | Test E | F Test | G Test | H Test |
|---|---|---|---|---|---|
| I | Glyceryl Stearate (and) Ceteareth-20(and) Ceteareth 12 (and) Cetearyl Alcohol (and) Cetyl Palmitate | 6.00 | 6.00 | 6.00 | 6.00 |
| I | Cetearyl Alcohol | 0.50 | 0.50 | 0.50 | 0.50 |
| I | Light Liquid Paraffin | 6.00 | 6.00 | 6.00 | 6.00 |
| I | Isopropyl Palmitate | 6.0 | 6.00 | 6.00 | 6.00 |
| I | Cocoyl Glyceryl Solketal | 3.00 | — | — | |
| I | C 12-C15 Alkyl Benzoate | — | 3.00 | — | |
| I | Dibutyl Adipate | — | — | 3.00 | — |
| I | Dicaprylyl Carbonate | — | — | — | 3.00 |
| II | Preservative | 0.30 | 0.30 | 0.30 | 0.30 |
| II | Water (qs) | 100 | 100 | 100 | 100 |

Procedure:

1.—Mix Phase I and heat to 80-85° C.

2.—Mix Phase II and heat to 80-85° C.

3.—Under stirring, add Phase II over Phase I.

4.—Cool under stirring to 30° C. and unload.

We carried out the performance test, where we evaluated the performance of the emollient in terms of the effectiveness of removing lipstick and makeup.

The Makeup Remover formulations were evaluated according to the protocol below:

1.—Apply the lipstick to the forearm, making a line on it.

2.—Apply the foundation, making a mark on it.

3.—Let it rest for 10 minutes.

4.—Remove it, with a non-woven cloth, moistened with 2 g of the makeup remover to be tested.

5.—Evaluate them, mentioning whether the emollient increased or decreased the removal power. Considering score 1 as decreasing and 2 as increasing.

6—Evaluate the sensorial aspects in terms of softness and smoothness. We used scales from 1 to 5; where 1=Bad and 5=Excellent.

TABLE 8

SENSORY EVALUATION IN SOFTNESS AND SMOOTHNESS REQUIREMENTS

| Assessment | Test E | Test F | Test G | Test H |
|---|---|---|---|---|
| Makeup Removal Power | 2 | 2 | 2 | 2 |
| Softness | 5 | 4 | 4 | 4 |
| Smoothness | 5 | 3 | 4 | 4 |

TABLE 9

ROLL ON DEODORANT

| Phase | Composition-INCI names | Test I | Test J | Test K | Test L |
|---|---|---|---|---|---|
| I. | Glyceryl Stearate (and) Ceteareth-20(and) | 2.1 | 2.1 | 2.1 | |
| | Ceteareth 12 (and) Cetearyl Alcohol (and) Cetyl Palmitate | | | | 2.1 |
| | Ceteareth-20 | 1.9 | 1.9 | 1.9 | 1.9 |
| | Glycerin Mono-Distearate | 2.0 | 2.0 | 2.0 | 2.0 |
| | Behenyl Alcohol | 1.0 | 1.0 | 1.0 | 1.0 |
| | Ethylhexyl Stearate | 1.7 | 1.7 | 1.7 | 1.7 |
| | Cocoyl Glyceryl Solketal | 1.7 | — | — | — |
| | C12-C15 Alkyl Benzoate | — | 1.7 | — | — |
| | Dibutyl Adipate | — | — | 1.7 | — |
| | Dicaprilyl Carbonate | — | — | — | 1.7 |
| II. | Edta Dissodico | 0.05 | 0.05 | 0.05 | 0.05 |
| | Distilled water (qs) | 100.0 | 100.0 | 100.0 | 100.0 |
| III. | Aluminum Sesquihydrochloride | 40.0 | 40.0 | 40.0 | 40.0 |
| IV. | Fragrance | 0.1 | 0.1 | 0.1 | 0.1 |

Process:

1.—Weigh phase I, heat it to 80° ° C.

2.—Weigh phase II, heat it to 80° C., add phase V over phase II.

3.—Pour phases II+V onto phase I.

4.—Cool the emulsion to 45° C., add phase III and then phase IV.

Protocol:

1.—10 volunteers.

2.—Application to the armpit.

Spreadability, absorption, oiliness, softness and smoothness are evaluated. We used scales from 1 to 5; wherein 1=Bad and 5=Excellent.

Formulations J, K and L were submitted to the sensory panel, compared to formula I, where the results are shown in the table below.

TABLE 10

SENSORY PANEL OF FORMULATIONS J, K and L WITH FORMULA I.

| Assessment | Tested | Test J | Test K | Test L |
|---|---|---|---|---|
| Spreadability | 5 | 3 | 3 | 4 |
| Absorption | 5 | 3 | 4 | 4 |
| Oiliness | 5 | 3 | 4 | 4 |
| Softness | 5 | 4 | 4 | 4 |
| Smoothness | 5 | 4 | 4 | 4 |

In all these formulations, Cocoil Glyceryl Solketal demonstrated its solubilizing and/or emollient characteristics in these cosmetic applications.

The invention claimed is:

1. A cosmetic or personal care formulation comprising:

(i) water; and (ii) a compound having Formula (I):

(I)

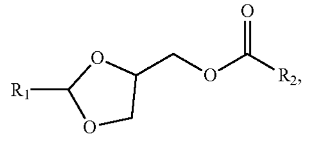

wherein:

$R_1$ is linear or branched alkyl having 3 to 8 carbons; and $R_2$ is linear or branched alkyl having 8 to 18 carbons.

2. The cosmetic or personal formulation of claim 1, wherein $R_2$ is derived from the oils and/or fatty acids of coconut, palm kernel, macauba, or babassu.

3. A cosmetic or personal care formulation comprising:

(i) water; and (ii) cocoyl glyceryl solketal.

4. The cosmetic or personal care formulation of claim 3, wherein the cosmetic or personal care formulation is an ultraviolet radiation protective body lotion, oil-free facial sunscreen, makeup remover, or antiperspirant deodorant.

5. The ultraviolet radiation protective body lotion of claim 4, further comprising a preservative.

6. The ultraviolet radiation protective body lotion of claim 5, further comprising a fragrance.

7. The ultraviolet radiation protective body lotion of claim 6, further comprising diethylamino hydroxybenzoyl hexyl benzoate.

8. The ultraviolet radiation protective body lotion of claim 7, further comprising disodium ethylenediaminetetracetic acid.

9. The ultraviolet radiation protective body lotion of claim 8, further comprising titanium dioxide, ethylhexyl methoxycinnamate, or a combination thereof.

10. The ultraviolet radiation protective body lotion of claim 9, further comprising caprylic and capric triglyceride.

11. The ultraviolet radiation protective body lotion of claim 10, further comprising cetearyl alcohol, glyceryl stearate, sodium cetearyl sulfate, or a mixture thereof.

12. The ultraviolet radiation protective body lotion of claim 4, wherein the lotion is prepared by:

(i) combining about 0.1 g xanthan gum and about 1 g glycerin to create a Phase I mixture;

(ii) combining about 0.05 g disodium ethylenediaminetetraacetic acid and about 0.5 g of mixture of acrylates and beheneth-25 methacrylate copolymer, and q.s. water to create a Phase II mixture;

(iii) adding the Phase II mixture to the Phase I mixture;

(iv) heating the Phase I and II mixture to about 80° C.-85° C.;

(v) combining about 5.5 g diethylamino hydroxybenzoyl hexyl benzoate, about 3 g cocoyl glyceryl solketal, about 3 g caprylic and capric triglyceride, about 2 g cetearyl alcohol, about 2 g glyceryl stearate, about 2 g sodium cetearyl sulfate, about 0.1 g BHT, and about 2 g of a mixture of titanium dioxide, hydrated silica, dimethicone/methicone copolymer, and aluminum hydroxide to create a Phase III mixture;

(vi) homogenizing and heating the Phase III mixture at about 80° C.-85° C.;

(vii) pouring the Phase I and Phase II mixture over the Phase III mixture under constant stirring;

(viii) adding aminomethyl propanol to the product of (vii) until the pH is from about 6.5 to about 7.0 to give a homogeneous emulsion (ix) combining about 0.3 g water and about 0.5 g of a mixture of methylene bis-benzotriazolyl tetramethylbutylphenol; water; decylglucoside, propylene glycol, and xanthan gum to create a Phase V mixture at a temperature below about 40° C.;

(x) adding the Phase V mixture to the homogeneous emulsion of (viii) while stirring;

(xi) adding about 0.6 g of fragrance and about 0.5 g of a mixture of phenoxyethanol, methylparaben, ethylparaben, propylparaben, butylparaben, and isobutylparaben to the mixture of (x);

(xii) homogenizing the mixture of (xi); and optionally (xiii) adjusting the pH of the mixture of (xii) between about 6.5 and about 8.5.

13. The oil-free facial sunscreen of claim 4, comprising a fragrance, sodium acrylate copolymer, cyclomethicone, aluminum starch octenylsuccinate, or a mixture thereof.

14. The oil-free facial sunscreen of claim 13, wherein the oil-free facial sunscreen is prepared by:

(i) combining about 2 g cocoyl glyceryl solketal, about 5 g diethylamino hydroxybenzoyl hexyl benzoate, about 8.5 g ethylhexyl methoxycinnamate, and about 3 g of a mixture of sodium acrylate copolymer, paraffinum liquid, and PPG-1 trideceth-6 to create a Phase I mixture;

(ii) combining about 0.05 g disodium ethylenediaminetetraacetic acid and q.s. water to create a Phase II mixture;

(iii) mixing Phase I mixture and Phase II mixture together and heating to about 80° C.-85° C. under constant stirring to give an emulsion;

(iv) combining about 6 g water and about 6 g of a mixture of methylene bis-benzotriazolyl tetramethylbutylphenol, water, decylglucoside, propylene glycol, and xanthan gum to create a Phase III mixture at a temperature below about 40° C.;

(v) adding the Phase III mixture to the emulsion of (iii) while stirring;

(vi) adding about 3 g cyclomethicone, about 3 g aluminum starch octenylsuccinate, about 0.3 g fragrance, and about 0.5 g of a mixture of phenoxyethanol, methylparaben, ethylparaben, propylparaben, butylparaben, and isobutylparaben to the mixture of (v);

(vii) homogenizing the mixture of (vi); and optionally (viii) adjusting the pH of the mixture of (vii) from about 6.5 to about 8.5.

15. The makeup remover of claim 4, comprising a preservative, glyceryl stearate, ceteareth-20, ceteareth-12, cetearyl alcohol, cetyl palmitate, paraffin, isopropyl palmitate, or a mixture thereof.

16. The makeup remover of claim 15, wherein the makeup remover is prepared by:

(i) combining about 3 g cocoyl glyceryl solketal, about 0.5 g cetearyl alcohol, about 6 g light liquid paraffin, about 6 g isopropyl palmitate, and about 6 g of a mixture of glyceryl stearate, ceteareth-20, ceteareth-12, cetearyl alcohol, and cetyl palmitate to create a Phase I mixture;

(ii) heating the Phase I mixture to about 80° C.-85° C.;

(iii) mixing about 0.3 g preservative and q.s. water to create a Phase II mixture;

(iv) heating the Phase II mixture to about 80° C.-85° C.;

(v) adding the mixture of Phase II to the mixture of Phase I while stirring; and (vi) cooling the mixture of (v) to 30° C. while stirring.

17. The antiperspirant deodorant formulation of claim 4, further comprising aluminum sesquihydrochloride.

18. The antiperspirant deodorant of claim 17, further comprising a fragrance.

19. The antiperspirant deodorant of claim 18, further comprising glyceryl stearate, ceteareth-20, behenyl alcohol, ethylhexyl stearate, or a mixture thereof.

20. The antiperspirant deodorant of claim 19, wherein the deodorant is prepared by:

(i) combining about 1.7 g cocoyl glyceryl solketal, about 1.9 g ceteareth-20, about 2 g glycerin mono-distearate, about 1 g behenyl alcohol, about 1.7 g ethylhexyl stearate, and about 2.1 g of a mixture of glyceryl stearate, ceteareth-20, ceteareth-12, cetearyl alcohol, and cetyl palmitate to create a Phase I mixture;

(ii) heating the Phase I mixture to about 80° C.;

(iii) combining about 0.05 g disodium ethylenediaminetetraacetic acid and q.s. water to create a Phase II mixture;

(iv) heating the Phase II mixture to about 80° C.;

(v) optionally adjusting the pH of the Phase II mixture;

(vi) adding the product of step (v) to the mixture of Phase I;

(vii) cooling the emulsion to about 45° C.;

(viii) adding about 40 g aluminum sesquihydrochloride to the product of step (vii); and (ix) adding about 0.1 g fragrance to the product of step (viii).

* * * * *